United States Patent
Rubin

(10) Patent No.: US 10,537,582 B2
(45) Date of Patent: *Jan. 21, 2020

(54) MULTIPHASIC CONTRACEPTIVE REGIMEN FOR ORAL COMBINATION DRUG FORMULATION OF PROGESTIN AND ESTROGEN

(71) Applicant: ARSTAT, INC., Flemington, NJ (US)

(72) Inventor: Arkady Rubin, Flemington, NJ (US)

(73) Assignee: ARSTAT, INC., Flemington, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/429,835

(22) Filed: Jun. 3, 2019

(65) Prior Publication Data

US 2019/0282587 A1    Sep. 19, 2019

Related U.S. Application Data

(63) Continuation of application No. 16/139,515, filed on Sep. 24, 2018, which is a continuation of application No. 15/926,407, filed on Mar. 20, 2018, now Pat. No. 10,111,887, which is a continuation of application No. 15/593,771, filed on May 12, 2017, now Pat. No. 9,925,199, which is a continuation of application No. 14/301,768, filed on Jun. 11, 2014, now Pat. No. 9,675,622, which is a continuation of application No. PCT/US2012/068235, filed on Dec. 6, 2012.

(60) Provisional application No. 61/570,007, filed on Dec. 13, 2011.

(51) Int. Cl.
| | |
|---|---|
| *A61K 31/567* | (2006.01) |
| *A61K 9/00* | (2006.01) |
| *A61K 31/565* | (2006.01) |
| *A61K 31/57* | (2006.01) |

(52) U.S. Cl.
CPC .......... *A61K 31/567* (2013.01); *A61K 9/0053* (2013.01); *A61K 31/565* (2013.01); *A61K 31/57* (2013.01)

(58) Field of Classification Search
CPC ..................................................... A61K 31/56
See application file for complete search history.

(56) References Cited

U.S. PATENT DOCUMENTS

| | | | |
|---|---|---|---|
| 3,969,502 | A | 7/1976 | Lachnit-Fixson |
| 4,962,098 | A | 10/1990 | Boissonneault |
| 5,888,543 | A | 3/1999 | Gast |
| 2001/0020015 | A1 | 9/2001 | Kafrissen et al. |
| 2005/0038006 | A1 | 2/2005 | Shangold et al. |
| 2005/0113350 | A1 | 5/2005 | Duesterberg et al. |
| 2007/0111975 | A1 | 5/2007 | Diliberti et al. |
| 2007/0207945 | A1 | 9/2007 | Ellman |
| 2009/0291927 | A1 | 11/2009 | Boissonneault |
| 2011/0274740 | A1 | 11/2011 | Diliberti et al. |

OTHER PUBLICATIONS

DelConte et al., Contraception, 1999;59:187-193.*
Communication Pursuant to Aricle 94(3) EPC for EP Application No. 12857354.0, dated Feb. 15, 2019, EPO, Rijswijk, Netherlands.
The European Search Report for EP Application No. 12857354.0 dated Oct. 7, 2015, EPO, Munich, Germany.
Van Vliet H, et al. "Biphasic versus triphasic oral contraceptives for contraception," Contraception, 2002, US, vol. 65, No. 5, pp. 321-324.
Benagiano G, Carrara S, Filippi V. Safety, efficacy and patient satisfaction with continuous daily administration of levonorgestrel/ethinylestradiol oral contraceptives. Patient Preference and Adherence. 2009;3:131-43.
Center for Drug Evaluation and Research. Application No. 21-241. Ortho Tri-Cyclen Lo® NDA Medical review; accessed at http://www.accessdata.fda.gov/drugsatfda_docs/nda/2002/021241_SOOO_ORTHO-Tri-CYCLENE_MEDR.pdf (reference on file).
Center for Drug Evaluation and Research. Application No. 21-544. Seasonale® NDA Medical review; accessed at http://www.accessdata.fda.gov/drugsatfda_docs/nda/2003/21-544_SEASONALE_Medr_P1.pdf (reference on file).
Dando TM and Curran MP. Low dose ethinylestradiol and levonorgestrel. Drugs 2005; 65 (16): 2299-2306.
Grimes DA. et al. Triphasic versus monophasic oral contraceptives for contraception. Cochrane Database of Systematic Reviews 2006, Issue 3. Art. No. CD003553.
Heger-Mahn D., et al. Combined ethinylestradiol/gestodene contraceptive patch: two-center, open-label study of ovulation inhibition, acceptability and safety over two cycles in female volunteers. European Journal of Contraception and Reproductive Health Care, 9:173-181, 2004.
International search report and written opinion of the corresponding PCT Application, PCT/US12/68235, dated Feb. 15, 2013.
Lalley JJ. Oral contraceptives overview. UMHS Jul. 2002 [online]. Accessed athttp://www.med.umich.edu/obgyn/resdir/contraception/OralContLalley.html (reference on file).
Pierson RA, et al. Ortho Evra/Evra versus oral contraceptives: follicular developmentand ovulation in normal cycles and after an intentional dosing error. Fertil Steril 2003; 80:34-42.
Van Vliet H, et al. Biphasic versus triphasic oral contraceptives for contraception: a Cochrane review. Human Reproduction (2002) 17 (4): 870-873.

* cited by examiner

*Primary Examiner* — San Ming R Hui
(74) *Attorney, Agent, or Firm* — M&B IP Analysts, LLC

(57) ABSTRACT

A method for contraception includes administering to a female daily, in a fourphasic dosing regimen during a time period of 24 successive days, an oral combination drug formulation of norethindrone acetate and ethinyl estradiol (EE), wherein doses in the second, third and fourth phases of the regimen increase by a predefined dose increment as compared to the corresponding doses administered during the previous phase, wherein the norethindrone acetate dose in the first phase is 1000 mcg, in the second phase is 1125 mcg, in the third phase is 1250 mcg, and in the fourth phase is 1375 mcg, wherein the EE dose in the first phase is 20 mcg, in the second phase is 22.5 mcg, in the third phase is 25 mcg, and in the fourth phase is 27.5 mcg, and wherein the fourphasic dosing regimen is followed by 4 days without norethindrone acetate and EE administration.

12 Claims, No Drawings

MULTIPHASIC CONTRACEPTIVE REGIMEN FOR ORAL COMBINATION DRUG FORMULATION OF PROGESTIN AND ESTROGEN

CROSS REFERENCE TO RELATED APPLICATIONS

This application is a continuation application of U.S. patent application Ser. No. 16/139,515 filed on Sep. 24, 2018, now allowed. The application Ser. No. 16/139,515 is a continuation of U.S. patent application Ser. No. 15/926,407 filed on Mar. 20, 2018, now U.S. Pat. No. 10,111,887 which is a continuation of U.S. application Ser. No. 15/593,771 filed on May 12, 2017, now U.S. Pat. No. 9,925,199, which is a continuation of U.S. application Ser. No. 14/301,768 filed on Jun. 11, 2014, now U.S. Pat. No. 9,675,622. The application Ser. No. 14/301,768 is a continuation of International Application No. PCT/US2012/068235 filed on Dec. 6, 2012, which claims priority from U.S. Provisional Application No. 61/570,007 filed on Dec. 13, 2011. The above-referenced applications are hereby incorporated by reference in their entirety.

TECHNICAL FIELD

The disclosure generally relates to a multiphasic contraceptive dosing regimen in females including administration of an oral combination drug formulation comprising progestin and estrogen with doses of progestin and estrogen gradually increasing between phases of the regimen, provided that the ratio of a daily dose of progestin to a daily dose of estrogen is maintained at a constant level during the entire dosing period.

BACKGROUND

Hormonal combined oral contraceptives (COCs) are administered annually to tens of millions of women. There are different types of COCs with various combinations of progestins and estrogens. All COCs may be classified into two categories: monophasic COCs and multiphasic COCs. The most common classes of multiphasic COCs utilize biphasic and triphasic treatment regimens with 2 and 3 segments (phases) of the active drug-taking interval (dosing period), respectively.

Most popular multiphasic regimens are developed as triphasic COCs with changes in hormonal combinations approximately every 7 days within a 21-day active drug-taking interval. In some COC brands, the amount of estrogen changes during such an active drug-taking interval with a constant progestin dose (e.g., Estrostep®), while in other brands the amount of progestin changes and the amount of estrogen remains the same (e.g., Ortho Tri-Cyclen®, Ortho Tri-Cyclen Lo®, Ortho-Novum 7/7/7®). In other COC brands, both amounts of progestin and estrogen change during the active drug-taking interval with an increase in both progestin and estrogen amounts in comparison to the starting dose (e.g., Triphasil®, Triadene®).

Increased progestin and/or estrogen levels during the dosing period mimic the hormonal changes occurring in a woman's menstrual cycle. The dosage increases, particularly close to end of the drug-taking interval, ensure better suppression of ovulation and desirable changes in the endometrium leading to a greater contraceptive efficacy and improved menstrual bleeding pattern (cycle control).

Relatively high progestin and/or estrogen levels during the second and third weeks of the dosing period were proven to be very instrumental in the reduction of the total exposure to hormonal contraceptives. A good example is a transition from a high dose monophasic contraceptive (Ortho-Cyclen®) delivering 250 mcg of norgestimate (NGM) and 35 mcg of ethinyl estradiol (EE) daily to a triphasic regimen with the same daily EE dose and reduced overall exposure to NGM (180 mcg, 215 mcg and 250 mcg in the first, second and third week of the dosing period, respectively). Since relatively higher levels of NGM were delivered when they were needed most (during $2^{nd}$ and $3^{rd}$ weeks), an adequate contraceptive efficacy and cycle control were maintained.

Monophasic COCs are often recommended as a first choice for women starting COC use.[1,2] The reason for this is that monophasic COCs have the same amount of estrogen and progestin throughout the treatment cycle, and thus they are less likely to cause side effects that stem from fluctuating hormone levels. Such estrogen-related side effects include, e.g., bloating, headache, nausea, mastalgia, leukorrhea, and hypertension; and progestin-related side effects include, e.g., mood swings, cyclic mastalgia, depression, fatigue, decreased libido, and weight gain.[3]

It would be therefore advantageous to provide multiphasic COCs that resolve the deficiencies of existing multiphasic combined oral contraceptives.

SUMMARY

As specified above, there is a great need in the art to develop safer hormonal combined oral contraceptives (COCs) which reduce the undesirable side effects of currently used multiphasic COCs. The various disclosed embodiments address these and other needs by providing a novel combined oral contraceptive (COC) regimen comprising administering an oral combination drug formulation comprising progestin and estrogen as a multiphasic dosing regimen with a constant ratio of a daily dose of progestin to a daily dose of estrogen during the entire dosing period. The contraceptive regimen of the present embodiments preserves the contraceptive efficacy of current multiphasic COCs, while reducing the undesirable side effects associated with variability of the hormone levels.

Specifically, one exemplary embodiment disclosed herein provides a method of contraception in which a progestin and an estrogen are administered as an oral combination drug formulation daily for 21-24 days as a multiphasic dosing regimen. A multiphasic dosing regimen includes several (e.g., two to four) phases with the duration of each phase ranging from 4 to 16 days. The doses of progestin and estrogen gradually increase between phases (e.g., with doses of each of the progestin and estrogen in each subsequent phase of the regimen increasing by 10%-50% as compared to the corresponding doses of the progestin and estrogen administered in the immediately preceding phase of the regimen), provided that the ratio of a daily dose of progestin to a daily dose of estrogen is maintained at a constant level during the 21-24 day dosing period.

The constant progestin-to-estrogen ratio employed by the regimen of the disclosed embodiments ensures a robust balance between hormonal activities of each component during the entire dosing period. This results in a better safety profile since unopposed increases in drug levels in the systemic circulation of any component lead to a greater incidence of hormone-related adverse events, (estrogen-related side effects such as, e.g., bloating, headache, nausea, mastalgia, leukorrhea, and hypertension; or progestin-related side effects such as, e.g., mood swings, cyclic mastalgia, depression, fatigue, decreased libido, and weight gain). A gradual increase in both progestin and estrogen daily doses between phases of the multiphasic dosing regimen of the disclosed embodiments can improve contraceptive efficacy and cycle control when compared to low-dose formulations serving as starting doses of the currently used multiphasic dosing regimens. The regimens disclosed herein also result in a reduced total exposure to progestin and estrogen during the entire dosing period and better safety profile when compared to a high-dose formulation serving as final doses of the currently used multiphasic dosing regimens.

Non-limiting examples of oral drug formulations that are useful in the disclosed method include, but are not limited to, an oral tablet, an oral capsule and an oral caplet. In all embodiments, one of the agents is a progestin. Non-limiting examples of useful progestins include, but are not limited to, norgestrel, levonorgestrel, norethindrone, norethindrone acetate norethisterone, norgestimate, medroxyprogesterone, desogestrel, gestodene, dienogest, nestorone, nomegestrol, drospirenone, trimegestone, chlormadinone, cyproterone, and therapeutically acceptable salts or derivatives thereof. In all embodiments, another agent that can be utilized is an estrogen. Non-limiting examples of useful estrogens include, e.g., ethinyl estradiol, mestranol, estradiol, and therapeutically acceptable salts or derivatives thereof.

The various disclosed embodiments may be applied to any multiphasic regimen with any number of distinct phases within a dosing period, and with any duration of a dosing period ranging from a typical 21-day dosing period to a 24-day dosing period.

The various disclosed embodiments are applicable to any progestin/estrogen combinations which are useful for contraception. In a preferred embodiment, the multiphasic oral contraceptive contains levonorgestrel (LNG) and ethinyl estradiol (EE). The monophasic formulations of these compounds (100 mcg of LNG in combination with 20 mcg of EE and 150 mcg of LNG in combination with 30 mcg of EE) have been tested in numerous clinical trials. The trials established an acceptable LNG-to-EE ratio (5:1) and determined minimal therapeutically effective doses of LNG and EE.[5] This ratio provides experimental basis for an efficacious and safe multiphasic LNG/EE contraceptive regimen.

In another embodiment, the multiphasic LNG/EE COC provides higher contraceptive efficacy and better cycle control when compared to a low-dose monophasic LNG/EE contraceptive regimen. The multiphasic LNG/EE COC also provides better safety profile when compared to a high-dose monophasic LNG/EE contraceptive regimen. Specific examples of the recommended multiphasic LNG/EE regimens are presented in the following sections. While the exact doses for each drug useful in the method may be determined in clinical trials, a safe and efficacious multiphasic oral contraceptive formulation with a robust balance between hormonal activities of each component is a novel method of combined oral contraception. A balanced multiphasic regimen covering 21-24 days of active drug-taking is a novel method as well.

In conjunction with the above methods, certain disclosed embodiments provide contraceptive kits and packages adapted for successive daily oral administration of the progestin/estrogen formulations at daily doses and following multiphasic regimens described herein. Non-limiting examples of useful kits are provided in the section, below.

DETAILED DESCRIPTION

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality.

In one embodiment, a method of contraception in which a progestin (also commonly referred to as progestogen) and an estrogen are administered to a female as an oral combination drug formulation. In an embodiment, the oral combination drug formulation is administered daily for 21-24 successive days as a multiphasic dosing regimen consisting of several (e.g., two to four) phases with the duration of each phase ranging from 4 to 16 days. The female treated by the disclosed formulation may be in a childbearing age.

The regimen disclosed herein can be used, for example, as a 28-day "treatment period" with the number of days of active drug taking ranging from 21 to 24 ("dosing period") followed by 4 to 7 days without progestin and estrogen (or any other contraceptive steroids) administration.

In all embodiments disclosed herein there are at least two different doses of each drug administered within the 21-24 day dosing period with the doses of a progestin and estrogen gradually increasing between phases (e.g., with doses of each of progestin and estrogen in each subsequent phase increasing by 10%-50% as compared to the corresponding doses administered during the immediately preceding phase), provided that the ratio of a daily dose of progestin to a daily dose of estrogen is maintained at a constant level during the entire dosing period.

According to the disclosed embodiments there are two to four different phases of the multiphasic dosing regimens with duration of each phase ranging from 4 to 16 days.

In one embodiment, the multiphasic (triphasic) dosing regimen consists of 21 days of dosing period, with the first 7 days at the lowest daily doses of the progestin and estrogen; the next 7 days at the intermediate daily doses of the progestin and estrogen; and the last 7 days at the highest daily doses of the progestin and estrogen, which dosing period is followed by 7 days without progestin and estrogen administration.

In another embodiment, the multiphasic (biphasic) dosing regimen consists of 21 days of dosing period, with the first 11 days at the lower daily doses of the progestin and estrogen; the next 10 days at the higher daily doses of the progestin and estrogen, which dosing period is followed by 7 days without progestin and estrogen administration.

In another embodiment, the multiphasic (biphasic) dosing regimen consists of 21 days of dosing period, with the first 14 days at the lower daily doses of the progestin and estrogen; the next 7 days at the higher daily doses of the progestin and estrogen, which dosing period is followed by 7 days without progestin and estrogen administration.

In yet another embodiment, the multiphasic (triphasic) dosing regimen consists of 24 days of dosing period, with the first 8 days at the lowest daily doses of the progestin and estrogen, the next 8 days at the intermediate daily doses of the progestin and estrogen, and the last 8 days at the highest daily doses of the progestin and estrogen, which dosing period is followed by 4 days without progestin and estrogen administration.

The oral combination drug formulations are preferably administered to females one time per day.

The first dose of the disclosed oral combination drug formulation can be administered, e.g., within 1-7 days after the onset of a menstrual period.

Non-limiting examples of oral drug formulations useful in the disclosed method include, for example, an oral tablet, an oral capsule, and an oral caplet. In all embodiments, one of the active agents in the oral combination drug formulation is a progestin. Non-limiting examples of useful progestins include, for example, norgestrel, levonorgestrel, norethindrone, norethindrone acetate, norethisterone, norgestimate, medroxyprogesterone, desogestrel, gestodene, dienogest, nestorone, nomegestrol, drospirenone, trimegestone, chlormadinone, cyproterone, and therapeutically acceptable salts or derivatives thereof.

In one embodiment, the progestin is levonorgestrel (LNG). In one embodiment, the dose of LNG ranges from 100 mcg to 150 mcg per oral combination drug formulation.

In another embodiment, the progestin is norethindrone acetate. In one embodiment, the dose of norethindrone acetate ranges from 1000 mcg to 1500 mcg per oral combination drug formulation.

In all embodiments, one of the active agents in the oral combination drug formulation is an estrogen. Non-limiting examples of useful estrogens include, e.g., ethinyl estradiol, mestranol, estradiol, and therapeutically acceptable salts or derivatives thereof.

In one embodiment, the estrogen is ethinyl estradiol (EE). In one embodiment, the dose of EE ranges from 20 mcg to 30 mcg per oral combination drug formulation.

In one embodiment, the ratio of the daily dose of progestin to the daily dose of estrogen ranges from 5:1 to 50:1.

In a preferred embodiment, the ratio of the daily dose of LNG to the daily dose of EE is 5:1.

In another preferred embodiment, the ratio of the daily dose of norethindrone acetate to the daily dose of EE is 50:1.

In a preferred embodiment, (i) 100 mcg of LNG in combination with 20 mcg of EE is administered daily during the first 7 days of the 21-day dosing period (cycle days 1-7), (ii) 125 mcg of LNG in combination with 25 mcg of EE is administered daily during the next 7 days of the 21-day dosing period (cycle days 8-14), and (iii) 150 mcg of LNG in combination with 30 mcg of EE is administered daily during the last 7 days of the 21-day dosing period (cycle days 15-21), followed by 7 days without progestin and estrogen administration.

In another preferred embodiment, (i) 112.5 mcg of LNG in combination with 22.5 mcg of EE is administered daily during the first 7 days of the 21-day dosing period (cycle days 1-7), (ii) 125 mcg of LNG in combination with 25 mcg of EE is administered daily during the next 7 days of the 21-day dosing period (cycle days 8-14), and (iii) 137.5 mcg of LNG in combination with 27.5 mcg of EE is administered daily during the last 7 days of the 21-day dosing period (cycle days 15-21), followed by 7 days without progestin and estrogen administration. In yet another embodiment, (i) 100 mcg of LNG in combination with 20 mcg of EE is administered daily during the first 11 days of the 21-day dosing period (cycle days 1-11), and (ii) 150 mcg of LNG in combination with 30 mcg of EE is administered daily during the next 10 days of the 21-day dosing period (cycle days 12-21), followed by 7 days without progestin and estrogen administration.

In a further embodiment, (i) 100 mcg of LNG in combination with 20 mcg of EE is administered daily during the first 14 days of the 21-day dosing period (cycle days 1-14), and (ii) 150 mcg of LNG in combination with 30 mcg of EE is administered daily during the next 7 days of the 21-day dosing period (cycle days 15-21), followed by 7 days without progestin and estrogen administration.

In another embodiment, (i) 100 mcg of LNG in combination with 20 mcg of EE is administered daily during the first 8 days of the 24-day dosing period (cycle days 1-8); (ii) 125 mcg of LNG in combination with 25 mcg of EE is administered daily during the next 8 days of the 24-day dosing period (cycle days 9-16), and (iii) 150 mcg of LNG in combination with 30 mcg of EE is administered daily during the next 8 days of the 24-day dosing period (cycle days 17-24), followed by 4 days without progestin and estrogen administration.

In another embodiment, (i) 1000 mcg of norethindrone acetate in combination with 20 mcg of EE is administered daily during the first 7 days of the 21-day dosing period (cycle days 1-7), (ii) 1250 mcg of norethindrone acetate in combination with 25 mcg of EE is administered daily during the next 7 days of the 21-day dosing period (cycle days 8-14), and (iii) 1500 mcg of norethindrone acetate in combination with 30 mcg of EE is administered daily during the last 7 days of the 21-day dosing period (cycle days 15-21), followed by 7 days without progestin and estrogen administration.

In yet another embodiment, (i) 1125 mcg of norethindrone acetate in combination with 22.5 mcg of EE is administered daily during the first 7 days of the 21-day dosing period (cycle days 1-7), (ii) 1250 mcg of norethindrone acetate in combination with 25 mcg of EE is administered daily during the next 7 days of the 21-day dosing period (cycle days 8-14), and (iii) 1375 mcg of norethindrone acetate in combination with 27.5 mcg of EE is administered daily during the last 7 days of the 21-day dosing period (cycle days 15-21), followed by 7 days without progestin and estrogen administration.

In a further embodiment, (i) 1000 mcg of norethindrone acetate in combination with 20 mcg of EE is administered daily during the first 11 days of the 21-day dosing period (cycle days 1-11), and (ii) 1500 mcg of norethindrone acetate in combination with 30 mcg of EE is administered daily during the next 10 days of the 21-day dosing period (cycle days 12-21), followed by 7 days without progestin and estrogen administration.

In another embodiment, (i) 1000 mcg of norethindrone acetate in combination with 20 mcg of EE is administered daily during the first 14 days of the 21-day dosing period (cycle days 1-14), and (ii) 1500 mcg of norethindrone acetate in combination with 30 mcg of EE is administered daily during the next 7 days of the 21-day dosing period (cycle days 15-21), followed by 7 days without progestin and estrogen administration.

In yet another embodiment, (i) 1000 mcg of norethindrone acetate in combination with 20 mcg of EE is administered daily during the first 8 days of the 24-day dosing period (cycle days 1-8); (ii) 1250 mcg of norethindrone acetate in combination with 25 mcg of EE is administered daily during the next 8 days of the 24-day dosing period (cycle days 9-16), and (iii) 1500 mcg of norethindrone acetate in combination with 30 mcg of EE is administered daily during the next 8 days of the 24-day dosing period (cycle days 17-24), followed by 4 days without progestin and estrogen administration.

The disclosed embodiments also provided contraceptive kits and packages adapted for successive daily oral administration of the progestin/estrogen formulations at daily doses and following multiphasic regimens described herein.

In one embodiment, a multiphasic contraceptive kit adapted for successive daily oral administration is provided. The kit comprises: (i) 21-24 separate daily dosage units, each dosage unit comprises a progestin and an estrogen and the ratio of the dose of progestin to the dose of estrogen is the same for all dosage units, and the dosage units are divided into two to four phases with 4 to 16 dosage units in each phase, the doses of each of the progestin and estrogen in each subsequent phase are increased by 10%-50% as compared to the corresponding doses of the progestin and estrogen in the immediately preceding phase; and (ii) optionally comprising 4-7 daily dosage units having no contraceptive steroids, and (iii) optionally comprising instructions for use.

In one specific embodiment, the multiphasic contraceptive kit adapted for successive daily oral administration is provided. The kit comprises: (i) 21 separate daily dosage units divided into three phases. The first phase contains 7 dosage units, each dosage unit comprising 100 mcg of levonorgestrel (LNG) and 20 mcg of ethinyl estradiol (EE); the second phase contains 7 dosage units, each dosage unit comprising 125 mcg of LNG and 25 mcg of EE, and the third phase contains 7 daily dosage units, each dosage unit comprising 150 mcg of LNG and 30 mcg of EE, and (ii) optionally comprises 7 daily dosage units having no contraceptive steroids, and (iii) optionally comprises instructions for use.

In another specific embodiment, the multiphasic contraceptive kit adapted for successive daily oral administration is provided. The kit comprises: (i) 21 separate daily dosage units divided into two phases. The first phase contains 11 dosage units, each dosage unit comprising 100 mcg of levonorgestrel (LNG) and 20 mcg of ethinyl estradiol (EE); and the second phase contains 10 dosage units, each dosage unit comprising 150 mcg of LNG and 30 mcg of EE, and (ii) optionally comprises 7 daily dosage units having no contraceptive steroids, and (iii) optionally comprises instructions for use.

In yet another specific embodiment, the multiphasic contraceptive kit adapted for successive daily oral administration is provided. The kit comprises: (i) 21 separate daily dosage units divided into two phases. The first phase contains 14 dosage units, each dosage unit comprising 100 mcg of levonorgestrel (LNG) and 20 mcg of ethinyl estradiol (EE); and the second phase contains 7 dosage units, each dosage unit comprising 150 mcg of LNG and 30 mcg of EE, and (ii) optionally comprises 7 daily dosage units having no contraceptive steroids, and (iii) optionally comprises instructions for use.

In another embodiment, the multiphasic contraceptive kit adapted for successive daily oral administration is provided. The kit comprises: (i) 24 separate daily dosage units divided into three phases. The first phase contains 8 dosage units, each dosage unit comprising 100 mcg of levonorgestrel (LNG) and 20 mcg of ethinyl estradiol (EE); the second phase contains 8 dosage units, each dosage unit comprising 125 mcg of LNG and 25 mcg of EE, and the third phase contains 8 daily dosage units, each dosage unit comprising 150 mcg of LNG and 30 mcg of EE, and (ii) optionally comprises 4 daily dosage units having no contraceptive steroids, and (iii) optionally comprises instructions for use.

In yet another embodiment, the multiphasic contraceptive kit adapted for successive daily oral administration is provided. The kit comprises: (i) 21 separate daily dosage units divided into three phases. The first phase contains 7 dosage units, each dosage unit comprising 1000 mcg of norethindrone acetate and 20 mcg of ethinyl estradiol (EE); the second phase contains 7 dosage units, each dosage unit comprising 1250 mcg of norethindrone acetate and 25 mcg of EE, and the third phase contains 7 daily dosage units, each dosage unit comprising 1500 mcg of norethindrone acetate and 30 mcg of EE, and (ii) optionally comprises 7 daily dosage units having no contraceptive steroids, and (iii) optionally comprises instructions for use.

In a further embodiment, the multiphasic contraceptive kit adapted for successive daily oral administration is provided. The kit comprises: (i) 21 separate daily dosage units divided into two phases. The first phase contains 11 dosage units, each dosage unit comprising 1000 mcg of norethindrone acetate and 20 mcg of ethinyl estradiol (EE); and the second phase contains 10 dosage units, each dosage unit comprising 1500 mcg of norethindrone acetate and 30 mcg of EE, and (ii) optionally comprises 7 daily dosage units having no contraceptive steroids, and (iii) optionally comprises instructions for use.

In another embodiment, the multiphasic contraceptive kit adapted for successive daily oral administration is provided. The kit comprises: (i) 21 separate daily dosage units divided into two phases. The first phase contains 14 dosage units, each dosage unit comprising 1000 mcg of norethindrone acetate land 20 mcg of ethinyl estradiol (EE); and the second phase contains 7 dosage units, each dosage unit comprising 1500 mcg of norethindrone acetate and 30 mcg of EE, and (ii) optionally comprises 7 daily dosage units having no contraceptive steroids, and (iii) optionally comprises instructions for use.

In yet another embodiment, the multiphasic contraceptive kit adapted for successive daily oral administration is provided. The kit comprises: (i) 24 separate daily dosage units divided into three phases. The first phase contains 8 dosage units, each dosage unit comprising 1000 mcg of norethindrone acetate and 20 mcg of ethinyl estradiol (EE); the second phase contains 8 dosage units, each dosage unit comprising 1250 mcg of norethindrone acetate and 25 mcg of EE, and the third phase contains 8 daily dosage units, each dosage unit comprising 1500 mcg of norethindrone acetate and 30 mcg of EE, and (ii) optionally comprises 4 daily dosage units having no contraceptive steroids, and (iii) optionally comprises instructions for use.

The active compounds of the disclosed embodiments can be formulated in an oral combination drug formulation in combination with one or more pharmaceutically acceptable carriers and/or excipients such as, for example, stabilizers, lubricants, diluents, flavorants, colorants, buffers, and disintegrants. Suitable pharmaceutically acceptable carriers include any and all conventional solvents (e.g., water, physiological solution, dextrose, glycerol, ethanol, and the like, as well as combinations thereof), wetting agents, emulgators, buffers, conservants, antioxidants, dispersion media, fillers, solid carriers, coatings, antibacterial and antifungal agents, isotonic and absorption delaying agents, as well as other well-known agents which enhance the shelf life or effectiveness of one or more of the active components of the composition. Examples of such useful substances can be found, for example, in the book Remington: the science and practice of pharmacy. Lippincott Williams & Wilkins 2005. Except insofar as any conventional media or agent is incompatible with the active ingredients, use thereof in compositions of the present invention is contemplated.

It will be readily evident to one of ordinary skill that the various approaches useful in preparing pharmaceutical formulations, as described herein, and other approaches known in the art, may be combined in a single oral combination drug formulation.

Contraceptive kits and packages disclosed herein can be prepared following methods and designs well known in the art with appropriate daily dosage units (e.g., tablets, capsules, or caplets) arranged in a fixed sequence corresponding to various phases of a given administration regimen. Kits can optionally comprise instructions for use. Also, non-contraceptive dosage units may be optionally included in a kit for the remaining days of the 28-day cycle. Such non-contraceptive dosage units may optionally contain an iron supplement (e.g., ferrous fumarate).

The various disclosed embodiments are also described and demonstrated by the following non-limiting examples. However, the use of these and other examples anywhere in the specification is illustrative only and in no way limits the scope and meaning of the disclosed embodiments or of any exemplified term. Likewise, the disclosed embodiments are not limited to any particular preferred embodiments described here. Indeed, many modifications and variations of the embodiments described here may be apparent to those skilled in the art upon reading this specification, and such variations can be made without departing from the disclosed embodiments in spirit or in scope. The disclosed embodiments are therefore to be limited only by the terms of the appended claims along with the full scope of equivalents to which those claims are entitled.

The various disclosed embodiments are particularly useful for multiphasic formulations of levonorgestrel (LNG) and ethinyl estradiol (EE). A number of popular COCs (Alesse®, Nordette®, Triphasil®, Seasonique®, Seasonale®, etc) employ these hormones. LNG is also administered as a contraceptive progestin-only pill (Norgeston®), as an emergency contraceptive (Plan B®), as a hormonal agent in the intrauterine contraceptive system (Mirena®), and as a component of the medication developed for the treatment of menopausal symptoms (Climara Pro®).

While EE is present in an overwhelming majority of other COCs, unique features of LNG contribute to the popularity of the LNG/EE combined oral contraceptives. LNG-containing COCs are proven to be efficacious and safe treatment options for millions of women electing hormonal contraception. There are huge clinical databases confirming contraceptive and non-contraceptive benefits of the LNG/EE COCs. Importantly, LNG is known for the lowest incidence of venous thromboembolism (VTE) when compared to other contraceptive progestins, such as gestodene, desogestrel and drospirenone.[4]

A combination of daily dose of 100 mcg LNG and 20 mcg of EE is approved in the US (Alesse®, Levlite® and their generic equivalents) and other countries. This LNG/EE dose can be used as a starting dose to be administered during the first phase of a multiphasic dosing regimen of the disclosed embodiments. Since a relatively greater contraceptive efficacy and better cycle control with acceptable safety profile are confirmed for a higher-dose COC containing 150 mcg LNG and 30 mcg of EE also marketed in the US and other countries (Nordette®, Levlen®, Microgynon® and their generic equivalents), this LNG/EE dose can be used as a maximal dose to be administered during the last phase of a multiphasic dosing regimen of the disclosed according to some embodiments. The LNG/EE ratio (5:1) which has been established and tested in numerous clinical trials[5] can be used as a constant ratio of a daily dose of progestin to a daily dose of estrogen during the entire dosing period in one of the regimens of the disclosed according to some embodiments.

As a first non-limiting example, available clinical data for a monophasic formulation of 100 mcg LNG/20 mcg EE suggest less-than-optimal performance of this COC. One study reported rates of presumptive ovulation exceeding 20%[6], i.e., much greater than a threshold of 10% routinely used in the testing of contraceptives.[7] In another clinical study, Pearl Index (a number of pregnancies per 100 woman-years of product use) was 1.7 times greater in 100 mcg LNG/20 mcg EE monophasic group when compared to a higher-dose monophasic regimen (150 mcg LNG/30 mcg EE). When the same formulations were administered as a continuous 91-day dosing regimen, pregnancy rates were 2 times greater in a low-dose group. In both cases, treatment with 100 mcg LNG/20 mcg EE resulted in contraceptive efficacy inferior to any approved combined oral contraceptive.[8] Cycle control of the low-dose LNG/EE formulation (as assessed by the incidence of inter-menstrual bleeding) is also inferior to most of marketed COCs.[9]

The disclosed embodiments hypothesize that there is a need for an increase in both progestin and estrogen doses for effective contraception and cycle control, while better safety can be provided by maintaining an optimal constant progestin-to-estrogen ratio during the entire dosing period.

The disclosed embodiment provides a triphasic LNG/EE regimen with the following dosing schedule: (a) 100 mcg of LNG in combination with 20 mcg of EE is administered daily during the first 7 days of the 21-day dosing period (cycle days 1-7), (b) 125 mcg of LNG in combination with 25 mcg of EE is administered daily during the next 7 days of the 21-day dosing period (cycle days 8-14), and (c) 150 mcg of LNG in combination with 30 mcg of EE is administered daily during the next 7 days of the 21-day dosing period (cycle days 15-21). The last 7 days of the treatment period (cycle days 22-28) are contraceptive steroid-free. The total dose of progestin and estrogen per proposed multiphasic regimen is 17% less when compared to a high-dose monophasic LNG/EE COC (Nordette®, Levlen®, Microgynon® and their generic equivalents).

As another non-limiting example, 112.5 mcg of LNG in combination with 22.5 mcg of EE is administered daily during the first 7 days of the 21-day dosing period (cycle days 1-7), 125 mcg of LNG in combination with 25 mcg of EE is administered daily during the next 7 days of the 21-day dosing period (cycle days 8-14), and 137.5 mcg of LNG in combination with 27.5 mcg of EE is administered daily during the next 7 days of the 21-day dosing period (cycle days 15-21). The last 7 days of the treatment period (cycle days 22-28) are contraceptive steroid-free.

As another non-limiting example, 100 mcg of LNG in combination with 20 mcg of EE is administered daily during the first 11 days of the 21-day dosing period (cycle days 1-11), 150 mcg of LNG in combination with 30 mcg of EE is administered daily during the next 10 days of the 21-day dosing period (cycle days 12-21). The last 7 days of the treatment period (cycle days 22-28) are contraceptive steroid-free.

As yet another non-limiting example, 100 mcg of LNG in combination with 20 mcg of EE is administered daily during the first 14 days of the 21-day dosing period (cycle days 1-14), 150 mcg of LNG in combination with 30 mcg of EE is administered daily during the next 7 days of the 21-day dosing period (cycle days 15-21). The last 7 days of the treatment period (cycle days 22-28) are contraceptive steroid-free.

As yet another non-limiting example, 100 mcg of LNG in combination with 20 mcg of EE is administered daily during the first 8 days of the 24-day dosing period (cycle days 1-8), 125 mcg of LNG in combination with 25 mcg of EE is administered daily during the next 8 days of the 24-day dosing period (cycle days 9-16), and 150 mcg of LNG in combination with 30 mcg of EE is administered daily during the next 8 days of the 24-day dosing period (cycle days 17-24). The last 4 days of the treatment period (cycle days 25-28) are contraceptive steroid-free.

As yet another non-limiting example, the triphasic norethindrone acetate/ethinyl estradiol regimen with the following dosing schedule: (a) 1000 mcg of norethindrone acetate in combination with 20 mcg of EE is administered daily during the first 7 days of the 21-day dosing period (cycle days 1-7), (b) 1250 mcg of norethindrone acetate in combination with 25 mcg of EE is administered daily during the next 7 days of the 21-day dosing period (cycle days 8-14), and (c) 1500 mcg of norethindrone acetate in combination with 30 mcg of EE is administered daily during the next 7 days of the 21-day dosing period (cycle days 15-21). The last 7 days of the treatment period (cycle days 22-28) are contraceptive steroid-free.

As yet another non-limiting example, 1125 mcg of norethindrone acetate in combination with 22.5 mcg of EE is administered daily during the first 7 days of the 21-day dosing period (cycle days 1-7), 1250 mcg of norethindrone acetate in combination with 25 mcg of EE is administered daily during the next 7 days of the 21-day dosing period (cycle days 8-14), and 1375 mcg of norethindrone acetate in combination with 27.5 mcg of EE is administered daily during the next 7 days of the 21-day dosing period (cycle days 15-21). The last 7 days of the treatment period (cycle days 22-28) are contraceptive steroid-free.

As yet another non-limiting example, 1000 mcg of norethindrone acetate in combination with 20 mcg of EE is administered daily during the first 11 days of the 21-day dosing period (cycle days 1-11), 1500 mcg of norethindrone acetate in combination with 30 mcg of EE is administered daily during the next 10 days of the 21-day dosing period (cycle days 12-21). The last 7 days of the treatment period (cycle days 22-28) are contraceptive steroid-free.

As yet another non-limiting example, 1000 mcg of norethindrone acetate in combination with 20 mcg of EE is administered daily during the first 14 days of the 21-day dosing period (cycle days 1-14), 1500 mcg of norethindrone acetate in combination with 30 mcg of EE is administered daily during the next 7 days of the 21-day dosing period (cycle days 15-21). The last 7 days of the treatment period (cycle days 22-28) are contraceptive steroid-free.

As yet another non-limiting example, 1000 mcg of norethindrone acetate in combination with 20 mcg of EE is administered daily during the first 8 days of the 24-day dosing period (cycle days 1-8), 1250 mcg of norethindrone acetate in combination with 25 mcg of EE is administered daily during the next 8 days of the 24-day dosing period (cycle days 9-16), and 1500 mcg of norethindrone acetate in combination with 30 mcg of EE is administered daily during the next 8 days of the 24-day dosing period (cycle days 17-24). The last 4 days of the treatment period (cycle days 25-28) are contraceptive steroid-free.

All patents, applications, publications, test methods, literature, and other materials cited herein are hereby incorporated by reference in their entirety as if physically present in this specification.

REFERENCES

[1] Grimes D A., et al. Triphasic versus monophasic oral contraceptives for contraception. Cochrane Database of Systematic Reviews 2006, Issue 3. Art. No.: CD003553.

[2] Van Vliet H, et al. Biphasic versus triphasic oral contraceptives for contraception: a Cochrane review. Human Reproduction (2002) 17 (4): 870-873.

[3] Lalley J J. Oral contraceptives overview. UMHS 2002 July [online]. Accessed at http://www.med.umich.edu/obgyn/resdir/contraception/OralContLalley.html (reference on file).

[4] Benagiano G, Carrara S, Filippi V. Safety, efficacy and patient satisfaction with continuous daily administration of levonorgestrel/ethinylestradiol oral contraceptives. *Patient Preference and Adherence.* 2009; 3:131-43.

[5] Dando T M and Curran M P. Low dose ethinylestradiol and levonorgestrel. Drugs 2005; 65 (16): 2299-2306.

[6] Pierson R A, et al. Ortho Evra versus oral contraceptives: follicular development and ovulation in normal cycles and after an intentional dosing error. Fertil Steril 2003; 80:34-42.

[7] Heger-Mahn D., et al. Combined ethinylestradiol/gestodene contraceptive patch: two-center, open-label study of ovulation inhibition, acceptability and safety over two cycles in female volunteers. European Journal of Contraception and Reproductive Health Care, 9:173-181, 2004.

[8] Center for Drug Evaluation and Research. Application Number 21-544. Seasonale® NDA Medical review; accessed at http://www.accessdata.fda.gov/drugsatfda_docs/nda/2003/21-544_SEASONALE_Medr_P1.pdf (reference on file).

[9] Center for Drug Evaluation and Research. Application No. 21-241. Ortho Tri-Cyclen Lo® NDA Medical review; accessed at http://www.accessdata.fda.gov/drugsatfda docs/nda/2002/021241 S000 ORTH O-TRI-CYCLENE MEDR.pdf (reference on file).

What is claimed is:

1. A method of contraception in a female, comprising:
   administering to the female daily, during a time period of 21 successive days, an oral combination drug formulation of a progestin and an estrogen,
   wherein the oral combination drug formulation is administered in a triphasic dosing regimen comprising three phases, wherein the duration of one phase is 5 days and the duration of another phase is 7 days, and the duration of yet another phase is 9 days, wherein doses of each of the progestin and estrogen in each subsequent phase of the regimen increase by a predefined dose increment as compared to the corresponding doses of the progestin and estrogen administered during immediately preceding phase of the regimen,
   wherein the ratio of a daily dose of progestin to a daily dose of estrogen is maintained at a constant level during the entire dosing period, wherein the progestin in the oral combination drug formulation is levonorgestrel (LNG), wherein the LNG dose in the first phase is 100 mcg, wherein the LNG dose in the second phase is 125 mcg, and wherein the LNG dose in the third phase is 150 mcg,
   wherein the estrogen in the oral combination drug formulation is ethinyl estradiol (EE), wherein the EE dose in the first phase is 20 mcg, wherein the EE dose in the second phase is 25 mcg, wherein the EE dose in the third phase is 30 mcg, and wherein the triphasic dosing regimen is followed by a time period of 7 days without progestin and estrogen administration.

2. The method of claim 1, wherein the oral combination drug formulation is in a form of any one of: an oral tablet, an oral capsule, and an oral caplet.

3. The method of claim 2, wherein the oral combination drug formulation with 100 mcg of LNG in combination with 20 mcg of EE is administered daily during the first 5 days, the oral combination drug formulation with 125 mcg of LNG in combination with 25 mcg of EE is administered daily during the next 7 days, and the oral combination drug formulation with 150 mcg of LNG in combination with 30 mcg of EE is administered daily during the next 9 days, wherein the dosing regimen is followed by 7 days without progestin and estrogen administration.

4. The method of claim 2, wherein the oral combination drug formulation with 100 mcg of LNG in combination with 20 mcg of EE is administered daily during the first 9 days, the oral combination drug formulation with 125 mcg of LNG in combination with 25 mcg of EE is administered daily during the next 7 days, and the oral combination drug formulation with 150 mcg of LNG in combination with 30 mcg of EE is administered daily during the next 5 days, wherein the dosing regimen is followed by 7 days without progestin and estrogen administration.

5. A method of contraception in a female, comprising:
administering to the female daily, during a time period of 24 successive days, an oral combination drug formulation of a progestin and an estrogen,
wherein the oral combination drug formulation is administered in a triphasic dosing regimen comprising three phases, wherein the duration of one phase is 6 days and the duration of another phase is 8 days, and the duration of yet another phase is 10 days, wherein doses of each of the progestin and estrogen in in each subsequent phase of the regimen increase by a predefined dose increment as compared to the corresponding doses of the progestin and estrogen administered during immediately preceding phase of the regimen,
wherein the ratio of a daily dose of progestin to a daily dose of estrogen is maintained at a constant level during the entire dosing period, wherein the progestin in the oral combination drug formulation is levonorgestrel (LNG), wherein the LNG dose in the first phase is 100 mcg, wherein the LNG dose in the second phase is 125 mcg, and wherein the LNG dose in the third phase is 150 mcg,
wherein the estrogen in the oral combination drug formulation is ethinyl estradiol (EE), wherein the EE dose in the first phase is 20 mcg, wherein the EE dose in the second phase is 25 mcg, wherein the EE dose in the third phase is 30 mcg, and wherein the triphasic dosing regimen is followed by a time period of 4 days without progestin and estrogen administration.

6. The method of claim 5, wherein the oral combination drug formulation is in a form of any one of: an oral tablet, an oral capsule, and an oral caplet.

7. The method of claim 6, wherein the oral combination drug formulation with 100 mcg of LNG in combination with 20 mcg of EE is administered daily during the first 6 days, the oral combination drug formulation with 125 mcg of LNG in combination with 25 mcg of EE is administered daily during the next 8 days, and the oral combination drug formulation with 150 mcg of LNG in combination with 30 mcg of EE is administered daily during the next 10 days, wherein the dosing regimen is followed by 4 days without progestin and estrogen administration.

8. The method of claim 6, wherein the oral combination drug formulation with 100 mcg of LNG in combination with 20 mcg of EE is administered daily during the first 10 days, the oral combination drug formulation with 125 mcg of LNG in combination with 25 mcg of EE is administered daily during the next 8 days, and the oral combination drug formulation with 150 mcg of LNG in combination with 30 mcg of EE is administered daily during the next 6 days, wherein the dosing regimen is followed by 4 days without progestin and estrogen administration.

9. A method of contraception in a female, comprising:
administering to the female daily, during a time period of 24 successive days, an oral combination drug formulation of a progestin and an estrogen,
wherein the oral combination drug formulation is administered in a triphasic dosing regimen comprising three phases, wherein the duration of one phase is 14 days and the duration of another phase is 6 days, and the duration of yet another phase is 4 days, wherein doses of each of the progestin and estrogen in in each subsequent phase of the regimen increase by a predefined dose increment as compared to the corresponding doses of the progestin and estrogen administered during immediately preceding phase of the regimen,
wherein the ratio of a daily dose of progestin to a daily dose of estrogen is maintained at a constant level during the entire dosing period, wherein the progestin in the oral combination drug formulation is levonorgestrel (LNG), wherein the LNG dose in the first phase is 100 mcg, wherein the LNG dose in the second phase is 125 mcg, and wherein the LNG dose in the third phase is 150 mcg,
wherein the estrogen in the oral combination drug formulation is ethinyl estradiol (EE), wherein the EE dose in the first phase is 20 mcg, wherein the EE dose in the second phase is 25 mcg, wherein the EE dose in the third phase is 30 mcg, and wherein the triphasic dosing regimen is followed by a time period of 4 days without progestin and estrogen administration.

10. The method of claim 9, wherein the oral combination drug formulation is in a form of any one of: an oral tablet, an oral capsule, and an oral caplet.

11. The method of claim 10, wherein the oral combination drug formulation with 100 mcg of LNG in combination with 20 mcg of EE is administered daily during the first 4 days, the oral combination drug formulation with 125 mcg of LNG in combination with 25 mcg of EE is administered daily during the next 6 days, and the oral combination drug formulation with 150 mcg of LNG in combination with 30 mcg of EE is administered daily during the next 14 days, wherein the dosing regimen is followed by 4 days without progestin and estrogen administration.

12. The method of claim 10, wherein the oral combination drug formulation with 100 mcg of LNG in combination with 20 mcg of EE is administered daily during the first 14 days, the oral combination drug formulation with 125 mcg of LNG in combination with 25 mcg of EE is administered daily during the next 6 days, and the oral combination drug formulation with 150 mcg of LNG in combination with 30 mcg of EE is administered daily during the next 4 days, wherein the dosing regimen is followed by 4 days without progestin and estrogen administration.

* * * * *